US010817725B1

(12) United States Patent
Jain

(10) Patent No.: US 10,817,725 B1
(45) Date of Patent: Oct. 27, 2020

(54) SPACE ROCKET MONITORING SYSTEM FOR GREENHOUSE GAS EMISSIONS

(71) Applicant: Rishi Iyer Jain, Los Altos, CA (US)

(72) Inventor: Rishi Iyer Jain, Los Altos, CA (US)

( * ) Notice: Subject to any disclaimer, the term of this patent is extended or adjusted under 35 U.S.C. 154(b) by 0 days.

(21) Appl. No.: 16/991,484

(22) Filed: Aug. 12, 2020

(51) Int. Cl.
| | |
|---|---|
| *H04M 1/725* | (2006.01) |
| *G06K 9/00* | (2006.01) |
| *G01S 19/47* | (2010.01) |
| *G01N 33/00* | (2006.01) |
| *B64G 3/00* | (2006.01) |
| *H04N 5/247* | (2006.01) |
| *H04N 7/18* | (2006.01) |

(52) U.S. Cl.
CPC ........... *G06K 9/00671* (2013.01); *B64G 3/00* (2013.01); *G01N 33/0036* (2013.01); *G01S 19/47* (2013.01); *H04M 1/725* (2013.01); *H04N 5/247* (2013.01); *H04N 7/18* (2013.01)

(58) Field of Classification Search
CPC .. G06K 9/00671; B64G 3/00; G01N 33/0036; G01S 19/47; H04M 1/725; H04N 5/247; H04N 7/18
USPC ........................................................ 348/135
See application file for complete search history.

(56) References Cited

PUBLICATIONS

Ulanzi Multi Phone Camera Lens Kit for iPhone 11 Pro Max with Phone Case, CPL Filter+10X 20X Macro+2X Telephoto +180° Fisheye Lens for iPhone 11 Pro Max Smartphone Accessories. Downloaded from https://www.amazon.com/ULANZI-Telephoto-Fisheye-Smartphone-Accessories/dp/B07Z22B54P on Aug. 12, 2020.

*Primary Examiner* — William C Vaughn, Jr.
*Assistant Examiner* — Jae N Noh
(74) *Attorney, Agent, or Firm* — Stephen E. Zweig

(57) ABSTRACT

System and method of implementing a Space Rocket monitoring system for greenhouse gas emissions during rocket flight, employing smartphone video cameras equipped with custom lens attachments, image deconvolution software, machine vision software, and the Tsiolkovsky Rocket Equation. The smartphone is equipped with custom optical lens attachments including a periscope that improves spatial separation (parallax) between camera images and a spectroscope that disperses incoming light from the combustion characteristics of the rocket exhaust according to wavelength and frequency of the light. A combination of image deconvolution software and machine vision software analyzes the images, and matches with existing rocket databases (which may be on remote servers), to identify key rocket characteristics. These are used, in the Tsiolkovsky Rocket Equation to compute rocket fuel expenditures. The software computes greenhouse gas emissions and presents the results using a graphical user interface that presents rocket flight images and corresponding analytics.

19 Claims, 8 Drawing Sheets

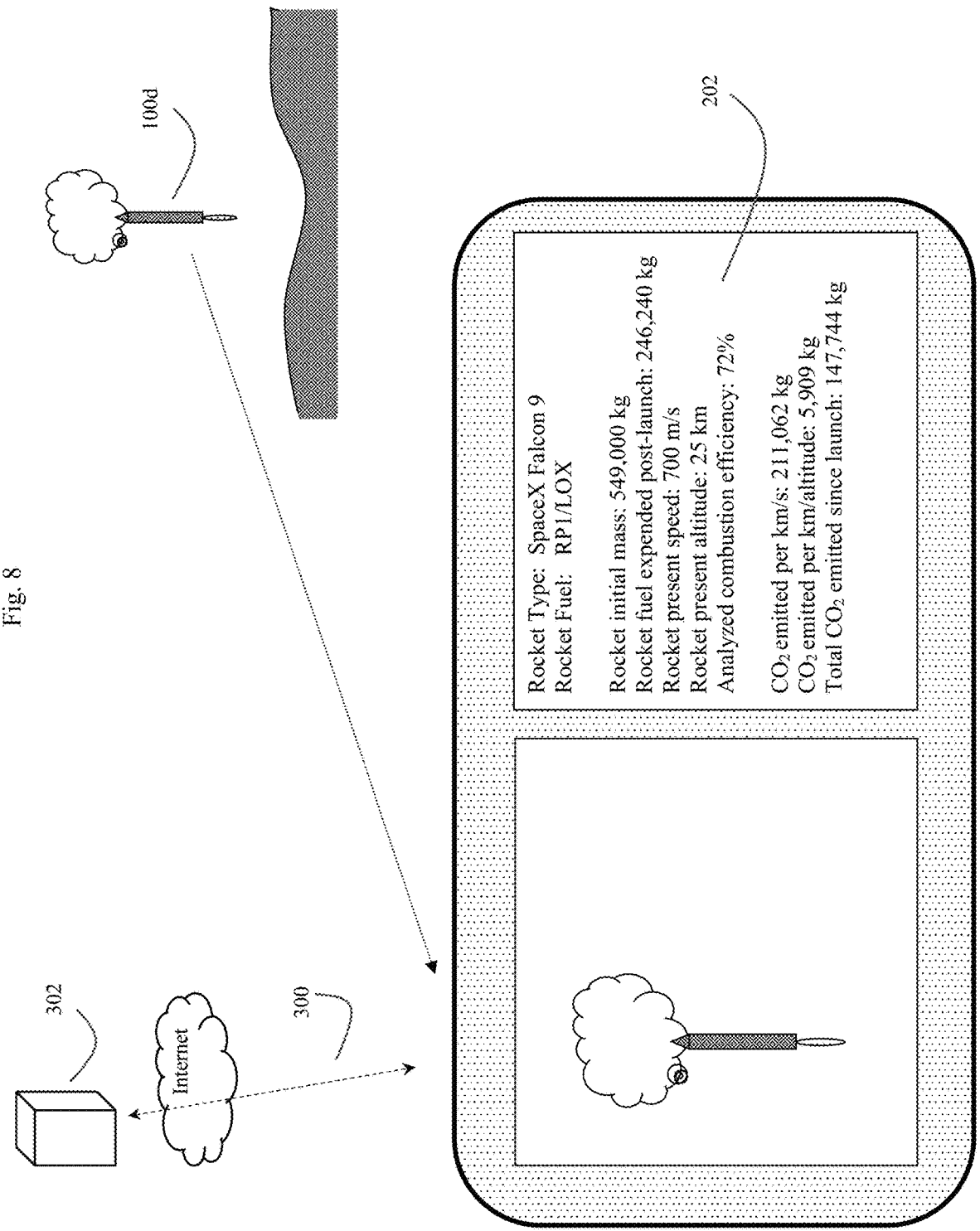

SPACE ROCKET MONITORING SYSTEM FOR GREENHOUSE GAS EMISSIONS

BACKGROUND OF THE INVENTION

Field of the Invention

This invention is in the field of methods and technologies to monitor greenhouse gas emissions.

Description of the Related Art

Global warming is a major ongoing ecological catastrophe, which over the next several generations is likely to undermine the health and safety of millions and perhaps billions of individuals. The problem is primarily caused by greenhouse gases, such as carbon dioxide ($CO_2$) and methane, which are produced by the burning of fossil fuels, agriculture, and other modern industrial processes. These cause the earth to warm, and ice caps to melt, resulting in a rise in sea levels, loss of valuable habitable and agricultural land, increase in deserts and unacceptably hot regions, and diminished agricultural output.

With the advent of cost-effective alternative energy sources, such as solar energy and wind energy, and advances in battery technology, technological solutions for greenhouse gas emissions are now available. However, such changes are slow and are often subject to changing political considerations.

Although methods for determining greenhouse gas emissions from power plants, internal combustion engines, and the like are known in the art, such methods often require specialized and expensive equipment. Specific less common greenhouse gas emission sources, such as rocket launches, are generally exempt from greenhouse gas regulations. For example, there is little prior art on greenhouse gas monitoring technology for rocket launches.

Smartphone technology: Modern smartphones, exemplified by the Apple 11 pro, often have multiple video cameras, as well as sophisticated processors, three-axis accelerometers, magnetic sensors to determine smartphone orientation, as well as high-resolution, touch-sensitive, display screens, and internet access using 4G or 5G cellular transceivers, as well as WIFI transceivers. Using the Apple 11 pro as an example, this particular model has three video cameras, mounted on the back, each equipped with a lens and a 12-megapixel color image sensor. The various lenses range from an f/2.4 wide ultra-wide-angle lens to an f/2.0 telephoto lens, to an f.1.8 wide-angle lens.

Since the Apple 11 pro has come out, various third-party manufacturers have provided smartphone cases with additional built-in lenses. These vendors include the Ulanzi corporation, Shenzhen, Guangdong, China, which produces the "U-Lens." This U-lens device comprises a smartphone camera case, equipped with various case mounted flip in lenses and filters to modify the optical characteristics of the standard iPhone 11 pro cameras.

BRIEF SUMMARY OF THE INVENTION

The invention was inspired, in part, by the insight that progress on controlling greenhouse gas emissions could be advanced if more people, in particular high school and college students, were made aware of the problem. The invention provides an inexpensive optical system and software method to convert standard smartphones into greenhouse gas monitoring systems for rocket launches.

The invention was also inspired, in part, on the insight that rocket launches are dramatic events. The invention provides a system and method that enables interested users to both observe rocket launches (or rocket landings), collect data, and calculate the likely amount of greenhouse gasses emitted.

Thus, in some embodiments, the invention may be a system or method to equip a standard smartphone, such as the iPhone 11 pro device, or other multiple camera smartphone devices, with additional optical equipment and software.

The invention enables the modified smartphone to monitor greenhouse emissions during a rocket flight.

In some embodiments, the invention may also be a method of configuring the smartphone's processor (such as a software method) to take data from the modified smartphone video cameras and use this data to compute greenhouse gas emissions.

More specifically, the invention may be a system and method of determining greenhouse gas emissions during rocket launches and landings. Here a multi-camera smartphone is equipped with a periscope attachment to improve spatial separation (parallax) between camera images.

The multi-camera smartphone is also equipped with a simplified imaging spectrograph. This is done by attaching a light spectrum dispersion attachment, such as a suitably oriented prism or diffraction grating arrangement to one of the smartphone video cameras. This spectrum dispersion attachment is configured to disperse incoming light (for example, from a rocket's exhaust) according to the wavelength or frequency of this light. This wavelength dispersed light is recorded by one of the smartphone's video cameras as a wavelength or frequency smeared image. The invention uses an unsmeared reference image (obtained from a different smartphone video camera), and image deconvolution software, to analyze this smeared image and determine, over various regions of the image, the spectral properties of the various portions of the image.

The high combustion regions of the rocket exhaust emit light according to the combustion reactions occurring in different regions of the rocket exhaust plume. The spectrum dispersion attachment thus allows the system to analyze the combustion characteristics of various parts of the rocket plume. These can be compared with reference combustion data, and summed up, on a rocket exhaust plume region by region basis, to attempt to determine the combustion characteristics of the rocket exhaust plume as a whole. This in turn can be used to estimate the amount of greenhouse gas emitted by the rocket exhaust plume.

The smartphone processor, optionally working with remote internet servers, can also use image recognition software (e.g., machine vision) to automatically analyze these images and identify the type of rocket in a rocket type and rocket characteristics database.

This database can also contain additional information about the rocket, such as the amounts and types of fuel and oxidizer. The database can also include other parameters such as rocket mass (when initially fueled, or when landed), rocket size dimensions (e.g., expected rocket length, which is useful for computing the distance between the smartphone and the rocket). The database can also contain tables of pre-computed hyperspectral characteristics of the rocket exhaust at various combustion efficiency levels. For example, lower efficiencies will typically be associated with longer frequency (redder) exhaust, while higher efficiencies will typically be associated with higher frequency (bluer) exhaust. This can allow the system to analyze combustion efficiency better, and thus the expected types of chemicals (e.g., greenhouse gasses, water vapor, unburned hydrocarbons, methane, and the like emitted by the rocket).

The processor can also use the optical data from the various video cameras to determine rocket velocity and rocket altitude as a function of time. Based on this information, the invention's software then uses a Tsiolkovsky Rocket Equation and information about rocket mass fuel types (as well as the specific impulse of that rocket's particular rocket engines) to solve for the probable amount of rocket fuel expenditure as a function of time. The system can then use the calculated fuel (and oxidizer) amounts expended, and the measured rocket exhaust combustion frequency, and the relation between combustion frequency and amount of greenhouse gas emitted, to determine the probable amount of the rocket's greenhouse gas emissions as a function of time, as well as a function of other parameters (rocket height, rocket velocity, etc.).

BRIEF DESCRIPTION OF THE DRAWINGS

FIG. 8 shows an example of how the invention can show both an image of the rocket (needed to assist the user in imaging the rocket), along with various additional information. This additional information can include the rocket's type and fuel, analyzed combustion efficiency, and amount of greenhouse gasses (here expressed in $CO_2$ equivalent values) during various phases of flight.

DETAILED DESCRIPTION OF THE INVENTION

The invention can be used to monitor greenhouse gas emissions during both rocket assents (takeoffs) and, for the latest reusable rocket boosters, rocket descents (landings) as well. Although in disclosure, SpaceX Falcon 9 rockets and Raptor engines have been used as examples, these examples are not intended to be limiting.

Figure 1:
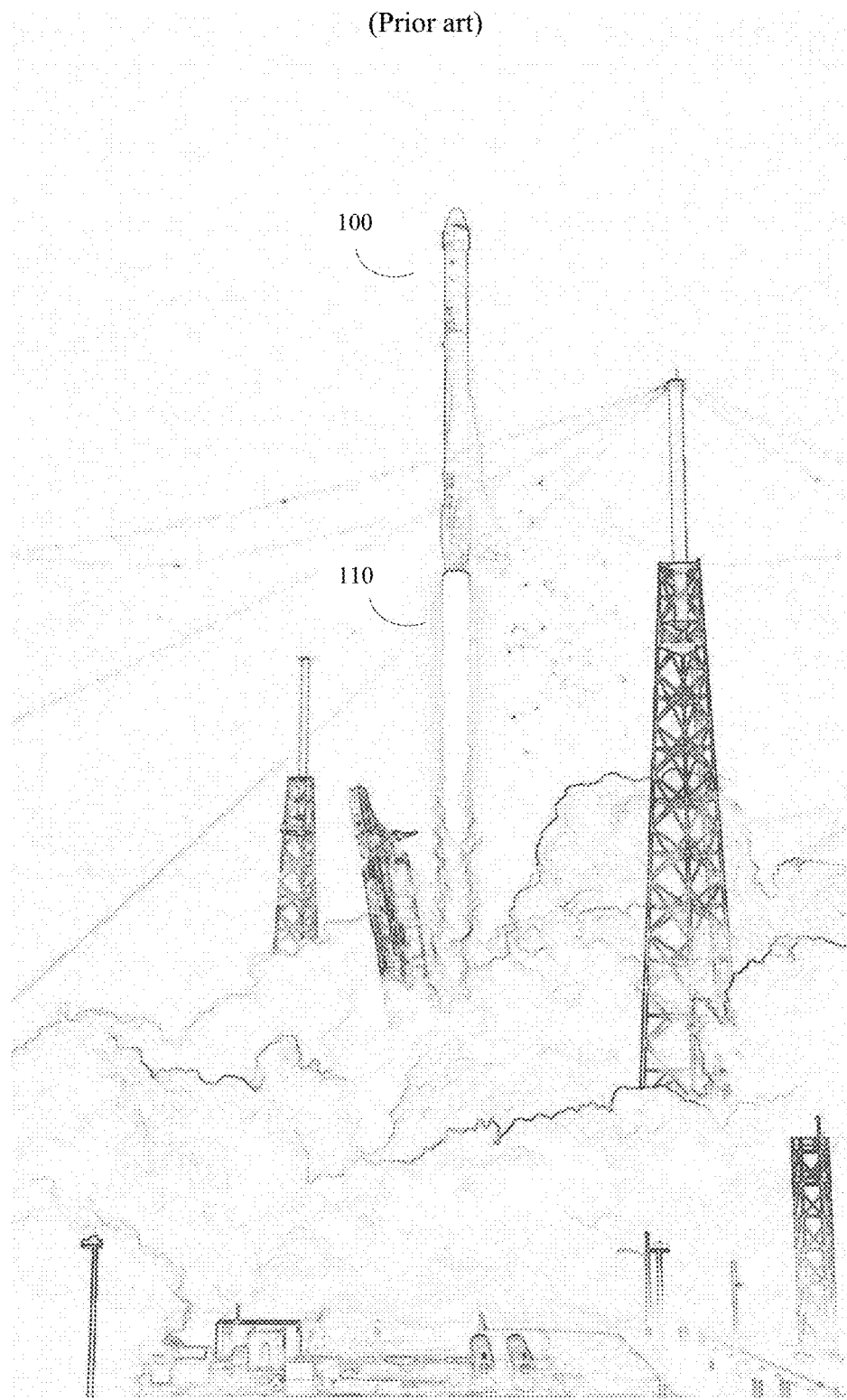
FIG. 1 shows an image of a rocket (here a SpaceX Falcon 9) on initial takeoff. The rocket itself has certain distinctive features, and the distribution of the rocket exhaust plume is also evident.

FIG. 1 shows an image of a rocket (here a SpaceX Falcon 9) on initial takeoff. Typically each rocket (100) has certain distinctive design features, which can be used to identify the rocket either visually, or by use of computerized vision systems. Note the distribution of the rocket exhaust plume (110). On takeoff, rocket engines are often throttled to different efficiency settings depending on the phase of the flight. For example, it is common to throttle rocket engines back while passing through the region of maximum dynamic pressure. Rocket engines also may be throttled to different extents depending on altitude, payload, presence or absence of side boosters, and other parameters. As a result, the relative amounts of greenhouse gasses emitted by the rocket can vary accordingly, depending on the flight phase.

Figure 2:
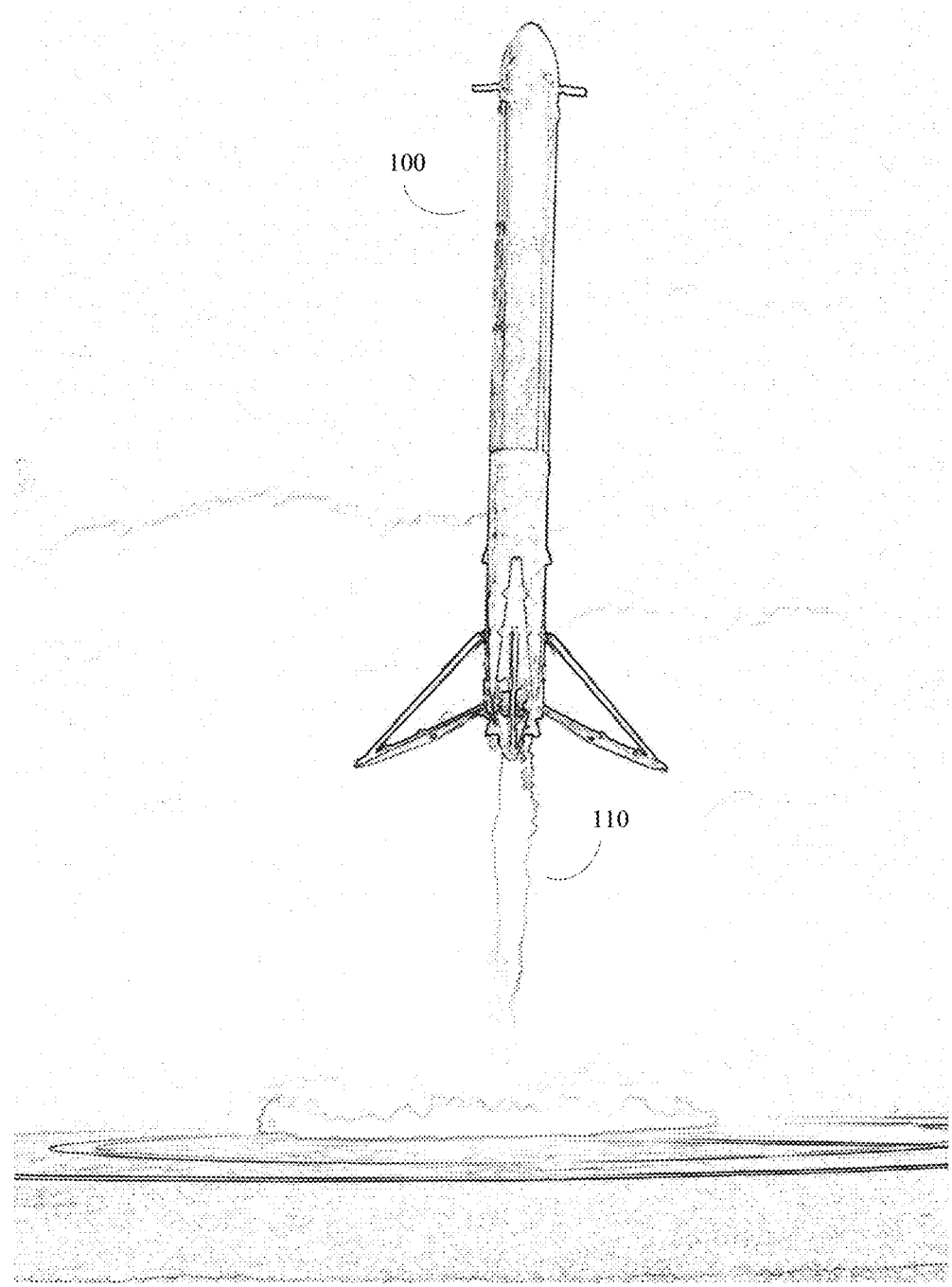
FIG. 2 shows an image of a rocket (a SpaceX Falcon 9 side booster from a Falcon 9 Heavy) landing.

FIG. 2 shows an image of a rocket (a SpaceX Falcon 9 side booster from a Falcon 9 Heavy) landing. Again, the rocket itself (100) has certain distinctive features. The distribution of the rocket exhaust plume (110), which is also evident, can vary between different landings. The fuel/oxidizer mixture and the combustion efficiency can also differ because the rocket engines need to throttle down and operate at a lower efficiency during landing. Using the Falcon 9 booster as an example, some landings operate on only one engine, some landings operate on all three engines. Each engine may throttle up and down according to wind conditions, the altitude of the rocket, speed of the rocket, distance to the landing zone, and other factors.

Figure 3:
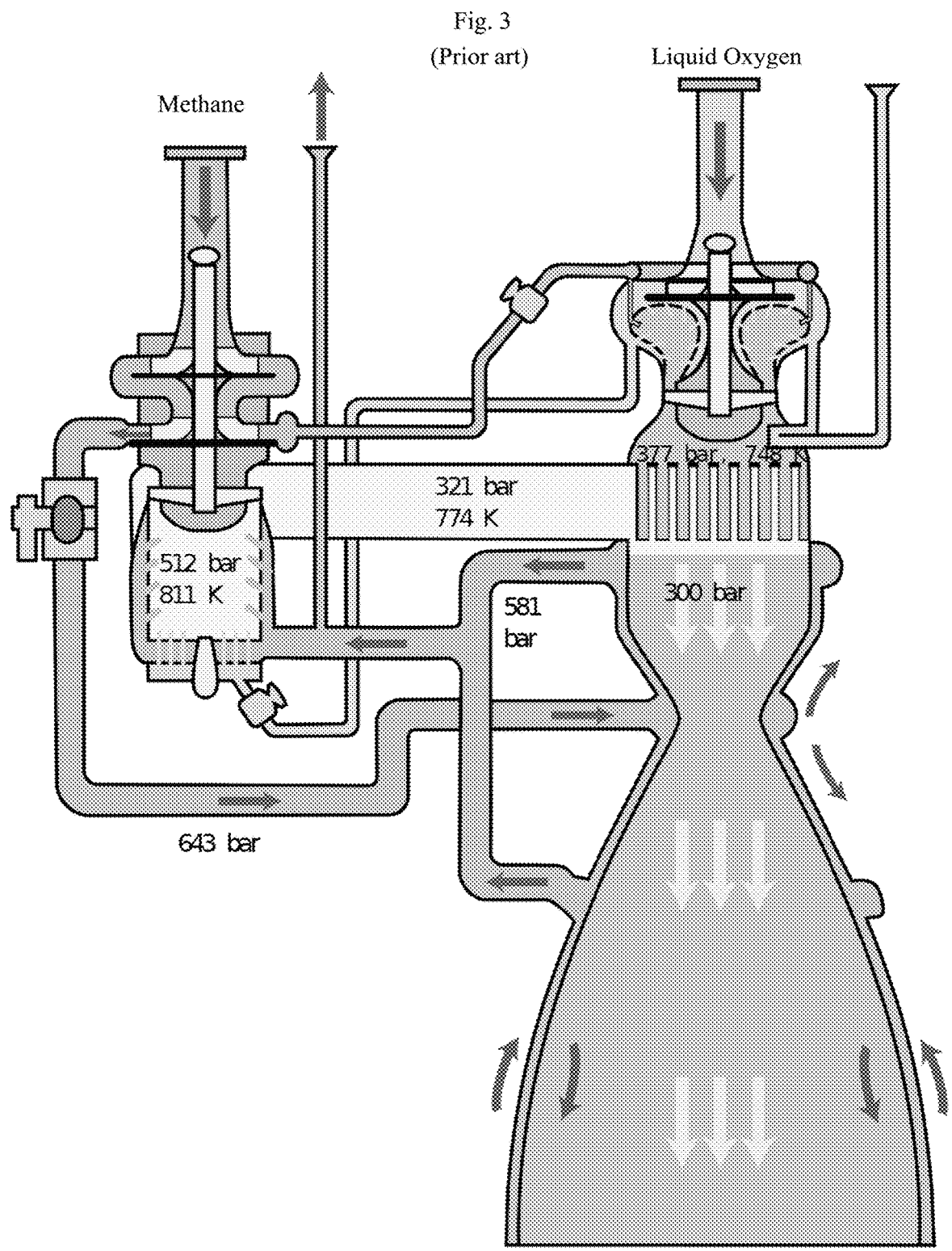
FIG. 3 shows a diagram of a more advanced SpaceX Raptor engine.

FIG. 3 shows a diagram of a more advanced SpaceX "Raptor" engine. This engine operates using liquid methane ($CH_4$), (which itself is a potent greenhouse gas) and liquid oxygen. RP1 (refined kerosene, which is a longer chain hydrocarbon) is a more common rocket fuel.

In contrast to a more traditional rocket fuel mixture, such as RP1/LOX, where lower combustion efficiency reduces the amount of $CO_2$ greenhouse gas emissions (because of a higher amount of longer chain hydrocarbons remaining in the exhaust), in a $CH_4$/LOX engine, lower combustion efficiency (resulting in more unburnt emitted $CH_4$ in the exhaust) may potentially increase the amount of greenhouse gas emissions. This is because $CH_4$ is a more potent greenhouse gas than $CO_2$.

As previously discussed, in some embodiments, the invention may be a device, system or method of determining greenhouse gas emissions during at least some phases of a rocket during flight. This is done by monitoring both the rocket and the rocket's exhaust plume.

As previously discussed, this method typically operates using a modified smartphone. As previously discussed, Apple 11 pro smartphones are used here as a specific example, but this example is not intended to be limiting. Other models of smartphones may also be used.

The smartphone will typically comprise (or be configured with) a front and a back. The front will usually have a GUI display (202), such as a touchscreen display. In a preferred embodiment, the back of the smartphone will typically comprise at least three video cameras. As will be discussed, the invention configures the smartphone to simultaneously obtain, over a plurality of time intervals, first viewpoint images and second viewpoint images of the rocket (and exhaust) as well as hyperspectral images of the rocket and the rocket exhaust.

The smartphone will typically further comprise at least one processor (the Apple 11 pro, for example, has a six-core A13 processor), memory, and at least one cellular or Wi-Fi wireless transceiver (which in turn may be used to connect to the internet). The smartphone will often contain other sensors, such as three-axis accelerometers, GPS receivers, and the like.

In a preferred embodiment of the invention, a first back-mounted video camera (often the camera's standard zoom lens camera) is used to image the rocket directly. These images are called "first viewpoint images". According to the invention, a second back-mounted video camera is typically configured with a periscope device or arrangement. Pictures taken by the second periscope equipped, back-mounted video camera are called "second viewpoint images." This periscope arrangement (or device) is configured to increase the spatial separation between the first viewpoint images and the second viewpoint images. Here a greater spatial separation allows the system to determine the distance to the rocket more accurately. This is because this increases parallax effects between the two cameras.

A third back-mounted video camera is typically configured with a spectrum dispersion device (essentially a crude, software-assisted, imaging spectroscope). This enables the third back-mounted camera to obtain spectrally convoluted images of the rocket and spectrally convoluted images of the rocket exhaust plume. As previously discussed, these images are "spectrally convoluted" in that the image is smeared according to the spectrum of the various parts of the image. See FIG. 5C for further discussion.

Figure 4A:
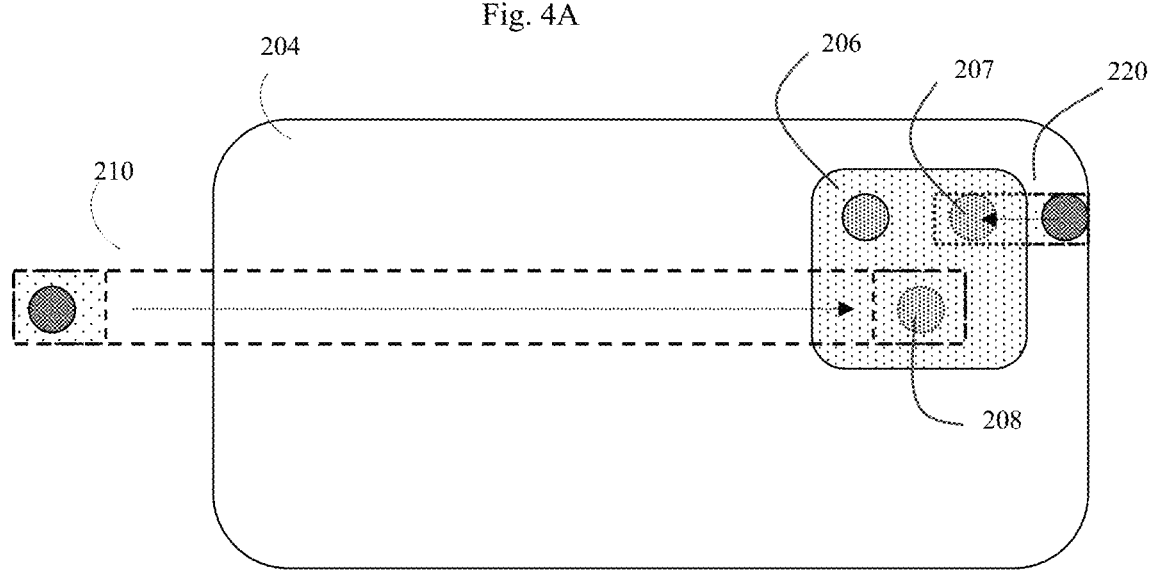
FIG. 4A shows the rear of a smartphone, with the invention's combination telescopic periscope and spectrum dispersion device, mounted on a smartphone case and attached over two of the smartphone's video camera lenses.

FIG. 4A shows the rear of a smartphone (204), with the invention's combination telescopic periscope (210) and spectrum dispersion device (220) mounted on a smartphone case (205) and attached over two (207, 208) of the smartphone's three video camera lenses (206, 207, 208).

Figure 4B:
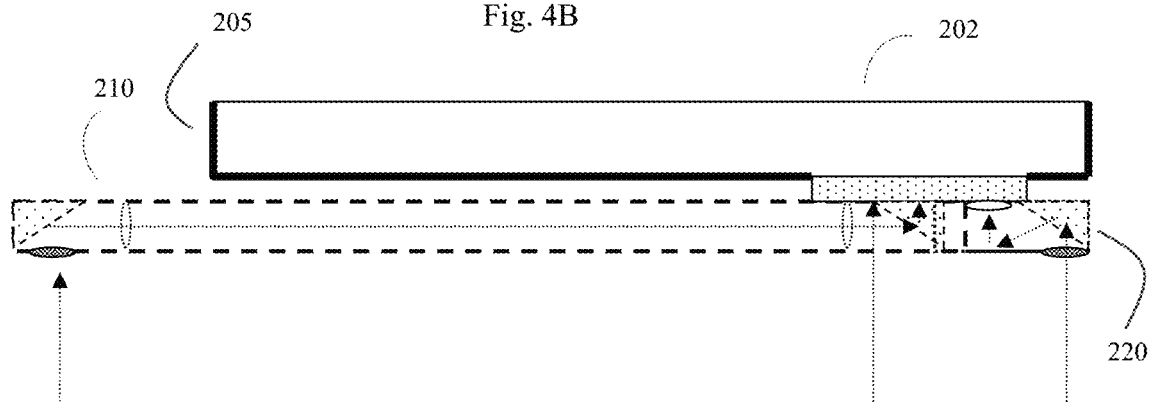
FIG. 4B shows the top view of the arrangement shown in FIG. 4A.

FIG. 4B shows the top view of the arrangement shown in FIG. 4A. Here the smartphone case (205) can be more clearly seen, as well as the light paths that incoming light takes as the light travels through the telescopic periscope (210), and through the spectrum dispersion device (220), and into the video camera lenses (208) and (207). Video camera and lens (206) are used to obtain normal (reference) images. Usually, video camera (206) will be the smartphone's telephoto lens camera, and additional (but optional) image magnifying lens arrangements are added to the telescopic periscope (210) and the light spectrum dispersion device (220) to obtain roughly equivalent magnification for all video cameras. The telescopic periscope attachment will typically contain angled mirrors to pass the signal from the far end of the periscope to the camera lens (208). In some embodiments, the telescopic periscope may be made extendible to extend still further away from lens (208) as desired.

In a preferred embodiment, periscope attachment (210) will have a length of at least six inches and is configured to increase a spatial separation between the first viewpoint images and the second viewpoint images by at least six inches. In a preferred embodiment, the periscope attachment may further comprise a periscope lens arrangement, configured to adjust the magnification of the second viewpoint images to match the magnification of the first viewpoint images.

Note that longer periscope attachment lengths are useful as well, which is why extendable embodiments are taught. In some embodiments, the periscope attachment may be a telescoping (e.g. variable length) periscope attachment that can be reduced in length for convenience while traveling, and can then be extended to still longer lengths, such as a foot length or more, while in use. This can improve distance measuring accuracy even further.

Figure 5A:
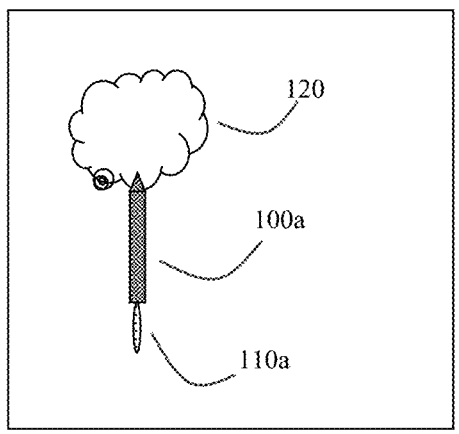
FIG. 5A shows an image of a rocket during launch, with a cloud in the background positioned behind the rocket.

FIG. 5A shows an image of a rocket (100a) during launch, with a cloud (120) in the background positioned behind the rocket. This image would be taken, for example, by the smartphone's standard built-in telephoto lens camera (206).

Figure 5B:
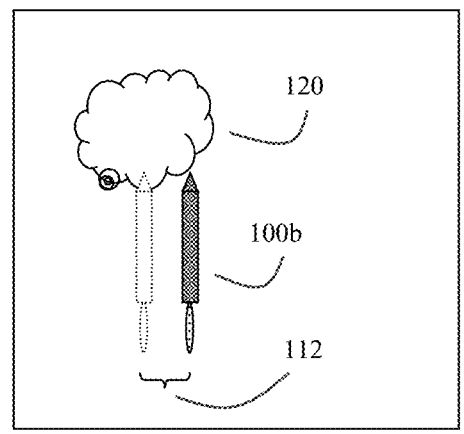
FIG. 5B shows a second image taken at the same time as FIG. 5A, of the same rocket during launch.

FIG. 5B shows a second image taken at the same time as FIG. 5A, of the same rocket during launch. The image in FIG. 5B can be made through the telescopic periscope attachment (210). Thus, due to parallax effects, the image of the rocket and its exhaust (foreground) appears displaced (112) versus the image of the background cloud. Here, the system software can use standard parallax determination calculations to determine distance, since the system will know various parameters, including separation between the first and second viewpoint images, size of the rocket, and the like.

Figure 5C:
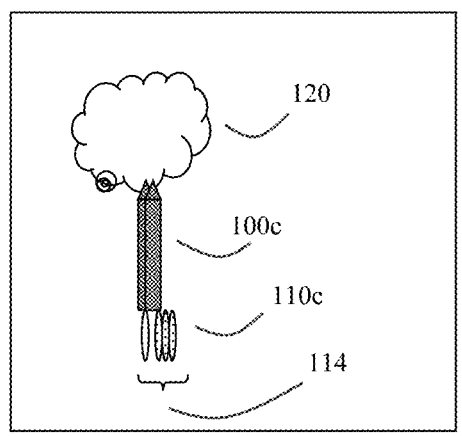
FIG. 5C shows a third image, taken through the spectrum dispersion device.

FIG. 5C shows a third image, taken through the spectrum dispersion device (220) by a camera (207). Here a prism or diffraction grating in the spectrum dispersion device partially separates the image according to the frequencies of the incoming light. The rocket exhaust (110a, 110c) will typically be the brightest part of this image. A cooler rocket exhaust will tend to emit lower frequency light, and thus its spectrally dispersed image will experience a smaller amount of spectral shift. By contrast, a hotter burning rocket exhaust (110a, 110c) will tend to emit higher frequency light, and thus its spectrally dispersed image will experience a higher amount of spectral shift (114). The net result is a somewhat blurry, spectrally convoluted image, that will be picked up by camera (207). The system can deconvolute this image (with the aid of reference image FIG. 5A), to determine the amount of spectral shift in various regions of the exhaust plume versus the FIG. 5A reference image. The system can then compare this spectral shift to reference combustion efficiency vs. spectral shift data, and thus experimentally determine some of the actual combustion characteristics of this particular rocket exhaust plume.

In a preferred embodiment, the periscope attachment (210) and the spectrum dispersion device (220) are both mounted on a case (205). This case (205) is configured to detachably snap on the back (204) of the smartphone, and over the three back-mounted video cameras (206, 207, 208). This arrangement thus positions the periscope attachment over a second video camera (208) and places the spectrum dispersion device over a third video camera (207).

In terms of software, typically, at least one processor will be configured to use at least one first viewpoint image (FIG. 5A from camera 206), and at least one second viewpoint image (FIG. 5B obtained using periscope device (210) and camera (208), and a parallax algorithm, to determine at least the distance to the rocket and exhaust plume. The system will often also determine the volume distribution of the rocket exhaust plume (110). Here "volume distribution" means the size of the exhaust plume and estimated volume of the exhaust plume.

To better estimate combustion efficiency, and thus amount of greenhouse gasses emitted, it is useful to determine a distance corrected hyperspectral map of the rocket exhaust. This is essentially a map of the distribution of the exhaust plume in three dimensions, with various regions where spectral data show combustion is proceeding at different efficiency levels.

In a preferred embodiment, the processor will use a deconvolution algorithm on the spectrally convoluted images of the rocket exhaust plume to determine the relative combustion efficiency of various regions of the plume. These results can then be corrected for the distance between the smartphone and the exhaust plume to determine the total size of different areas of the plume. To do this, the system will typically use either the first viewpoint images (FIG. 5A from camera 206), and/or the second viewpoint images (FIG. 5B from camera 208), and at least one spectrally convoluted image (FIG. 5C from camera 208) of the rocket (110*c*) and rocket exhaust (110*c*), and the deconvolution algorithm. The system then normalizes this result by distance to create distance corrected hyperspectral maps of the rocket exhaust plume.

Put alternatively, in some embodiments, the smartphone's processor, image recognition software, and the first (FIG. 5A) and the second viewpoint images (FIG. 5B) are used to determine a distance between the smartphone and the rocket and rocket exhaust. The processor also uses the spectrally convoluted images of the rocket and exhaust (FIG. 5C), deconvolute the spectrally convoluted images of the rocket and exhaust, thus producing a distance corrected hyperspectral map of the rocket exhaust plume. The system can then use image recognition software, various images of the rocket, and the distance to the rocket to retrieve information about rocket types from a database. This information can, for example, identify the type of rocket, as well as the rocket fuel types used by the rocket, the specific impulse of this fuel, and the fuel combustion characteristics of this rocket and fuel combination. Here "fuel" means fuel/oxidizer combination.

This information can be obtained by various methods. In some embodiments, the smartphone's processor uses the smartphone's wireless cellular or Wi-Fi transceivers to establish a wireless internet connection (see FIG. 8, 300) to a remote internet server and database (302). The smartphone processor can then automatically query the database (for example, with rocket shape characteristics obtained from imaging data), and download the information from the remote database (302).

In other embodiments, the user may enter the information directly on the smartphone's GUI display (e.g., touchscreen 202).

According to the invention, the smartphone can then use its processor, type of the rocket, distance to the rocket, and images of the rocket over a plurality of time intervals to determine a velocity of the rocket over at least some of plurality of time intervals. Here, for example, if the video cameras image at 60 frames per second, and the rocket moves a detectable distance between image frames, the distance to the rocket, and the amount of motion between frames, can be used to calculate the rocket's velocity directly.

The smartphone can also use its processor, the type of the rocket, rocket fuel type, the fuel combustion characteristics of the rocket, and the distance corrected hyperspectral map to determine a combustion efficiency of the rocket over at least some of the plurality of time intervals.

As a simplified example, consider a rocket exhaust plume operating at two different combustion efficiencies. For greater simplicity, assume that the combustion efficiency is evenly distributed throughout the plume. Then a plume from a rocket engine operating at lower combustion efficiency will tend to be at a lower temperature, and its spectral characteristics may tend towards longer wavelengths (towards the red). By contrast, a plume from a rocket engine operating at higher combustion efficiency will tend to be at a higher temperature, and its spectral characteristics may tend towards shorter wavelengths (towards the blue).

In a more realistic case, where the exhaust plume is non-uniform, the system can analyze different portions of the plume, from regions of the rocket engines operating at different combustion efficiencies. These different exhaust plume regions will emit light at different wavelengths. The smartphone processor can sum up the results from different areas of the rocket exhaust plume to create a summed (or integrated) value for the entire rocket exhaust plume.

Here, different fuel/oxidizer combinations will produce different wavelength combinations at different frequencies, and the system can download this data from the remote internet server (302).

The system can then use its one processor, the previously determined velocity, the previously obtained rocket fuel type, the calculated combustion efficiency, and a Tsiolkovsky rocket equation, to determine the amount of greenhouse gases emitted by the rocket over at least some of the various time intervals and rocket velocities. This method will generally tend to work best while the rocket is closest to the ground, where good initial mass estimates and image data are easier to obtain.

For example, one form of the Tsiolkovsky rocket equation is:

$$\Delta v = I_{sp} g_0 \ln \frac{m_0}{m_f},$$

where $\Delta v$ is a change in the velocity between a first-time interval and a second-time interval. $I_{sp}$ is a specific impulse of the rocket (which can be obtained from the server (302), and $m_0$ is an initial mass of the rocket, which can also be obtained from the server (302). Here the smartphone's processor solves for a final mass $m_f$ at the second time interval; and the amount of fuel expended between the first-time interval and the second time interval is $m_0 - m_f$.

Alternative Ways of Determining Distance:

In some embodiments, where the smartphone further comprises a GPS receiver and a three-axis accelerometer, the smartphone can use location data from its GPS receiver and smartphone tilt data from the three-axis accelerometer to compute the distance to the rocket by an alternative method.

Figure 6:
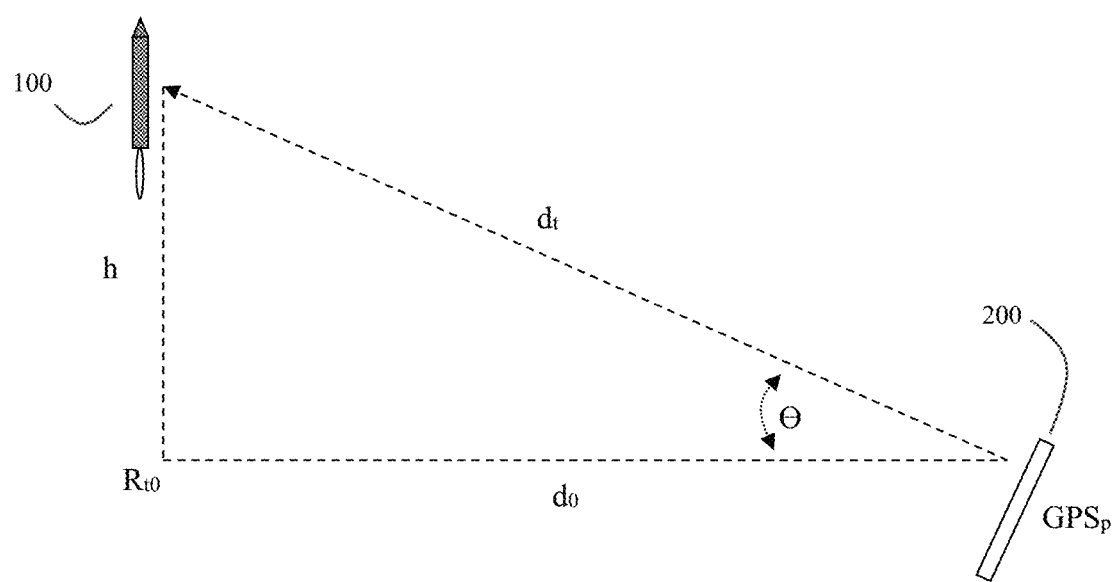
FIG. 6 shows how in some embodiments, at least when the initial launch or landing location of the rocket is precisely known, the system may optionally also determine the distance between the smartphone and the rocket, as well as the altitude of the rocket, by utilizing the smartphones GPS receiver to determine the location of the smartphone, and using the smartphone's three-axis accelerometer to determine the degree of tilt of the smartphone as it is imaging the rocket.

FIG. 6 shows how in some embodiments, at least when the initial launch or landing location of the rocket is precisely known, the system may optionally also determine the distance between the smartphone (200) and the rocket (100), as well as the altitude of the rocket (h), by utilizing the smartphones GPS receiver to determine the location of the smartphone. The system can then use, the smartphone's three-axis accelerometer to determine the degree of tilt ($\Theta$) of the smartphone as it is imaging the rocket. Thus the distance to the rocket at time "t" is $$d_t = \frac{d_o}{\text{Cos}(\theta)},$$

where $d_0$ is the distance between the known location of the rocket launch site or landing site, and the GPS location of the smartphone, and $\Theta$ is the angle of the smartphone. Similarly, the height of the rocket at any given time is $$h = d_0 \frac{\text{Sin}(\theta)}{\text{Cos}(\theta)}.$$

Determining the Amount of Greenhouses Produced:

typically, the smartphone will calculate the amount of greenhouse gasses emitted by the rocket by using the processor to multiply the combustion efficiency (or more precisely, the combustion efficiency of producing greenhouse gas emissions of the rocket engines) by the amount of fuel expended (as per the Tsiolkovsky rocket equation). The smartphone will then usually display this amount of greenhouse gases on its GUI display (202).

Figure 7:
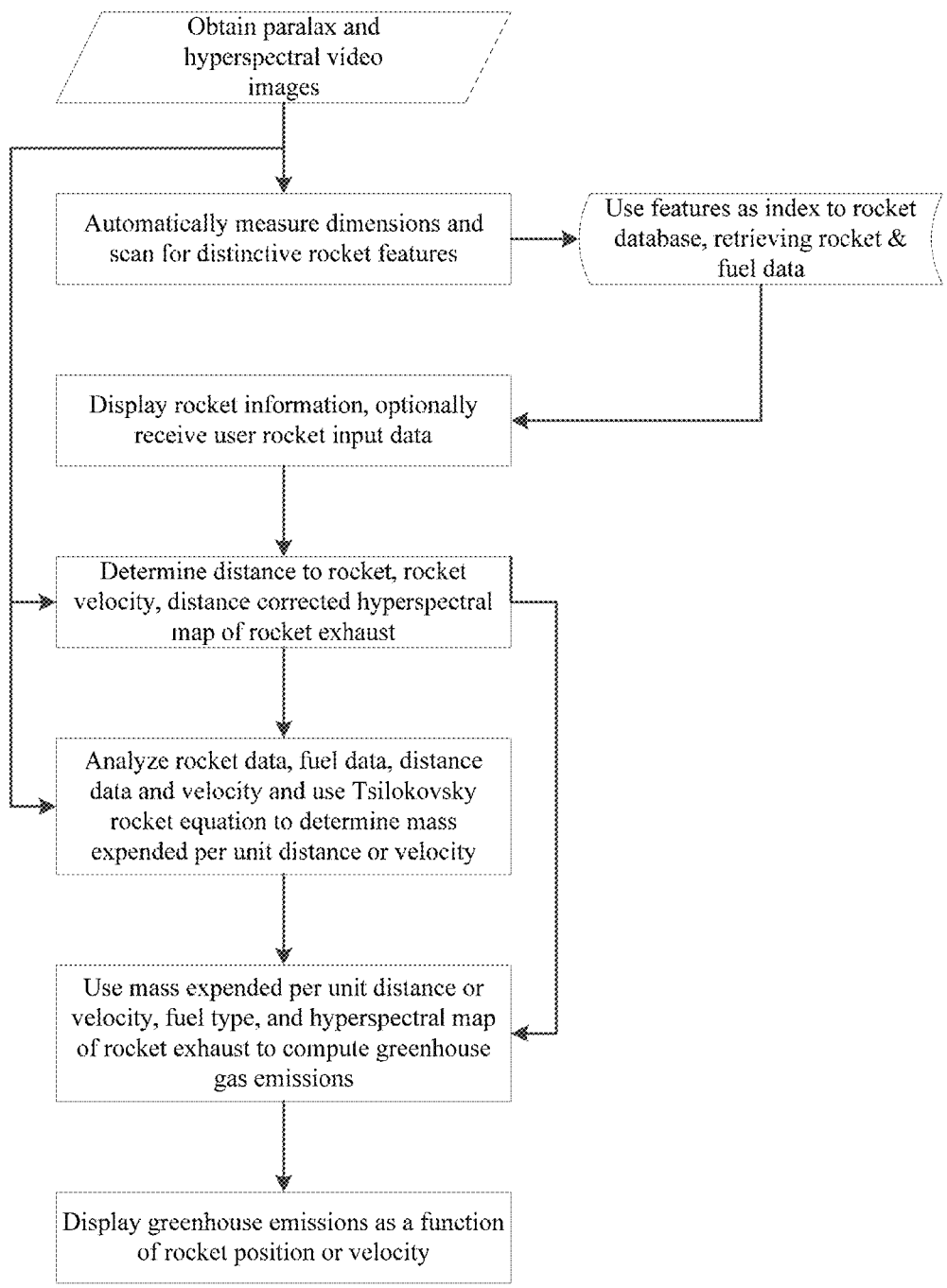
FIG. 7 shows a simplified flow chart showing some aspects of the invention's software.

FIG. 7 shows a simplified flow chart showing some aspects of the invention's software.

The software may be implemented as a downloadable smartphone app running on a smartphone processor, under the control of the smartphone's operating system (such as iOS or Android). Examples of suitable machine vision software, and machine learning image analysis software includes the Apple Vision framework, which is available for iOS version 11.0+ and higher. Other software methods, including TensorFlow, Amazon AWS deep learning system, or open source machine vision software such as SimpleCV may also be used.

In some embodiments, the software may implement some functions through an internet connection (300) to one or more remote servers, such as the server (302) shown in FIG. 8. Processors and databases on remote servers (302) can, for example, contain databases of relevant rocket data that the smartphone app can call upon as needed. Additionally, in some embodiments, machine vision or machine learning algorithms running on remote servers (302) can perform at least some of the more computationally intensive steps of these algorithms as desired.

FIG. 8 shows an example of how the invention can show an image of the rocket (needed to assist the user in properly imaging the rocket), along with various additional information. This additional information can comprise information about the rocket's type and fuel, the current status of the rocket, the analyzed combustion efficiency, and the amount of greenhouse gasses (here expressed in $CO_2$ equivalent values) during various phases of flight.

Further Details:

In some embodiments, the smartphone processor further analyzes the distance-corrected hyperspectral map of the rocket exhaust (110) to determine any of a distance-corrected chemical composition map of the rocket exhaust, and a distance-corrected temperature composition map of the rocket exhaust.

To further calculate combustion efficiency, the processor then can analyze this distance-corrected chemical composition map of the rocket exhaust (and/or the distance-corrected temperature composition map of the rocket exhaust), versus any of a formula or database of chemical composition and/or temperature versus the combustion efficiency for the rocket fuel type.

This analysis can be as simple as, over each region of the exhaust plume map, and on a region-by region basis, looking up the combustion efficiency of this portion of the rocket exhaust plume (using the formula or table data), using the properties of each region to determine the combustion efficiency (on a mass adjusted basis) of that region. The various regions can then be summed up over the entire plume map to calculate the combustion efficiency of the rocket engine over a given time interval.

In some embodiments, for rocket launches, the system can further be configured to sum up the amount of greenhouse gases over the plurality of time intervals from the initial launch of the rocket up to a predetermined speed or altitude. Similarly, for rocket landings, the system can be configured to sum up the amount of greenhouse gases emitted by the rocket starting from a predetermined rocket entry speed or rocket entry altitude, to the time the rocket lands.

Put alternatively, in some embodiments, the combustion efficiency can be determined by using the processor to compare the distance corrected hyperspectral map of the rocket exhaust against a plurality of reference hyperspectral data of the rocket fuel type, and the fuel combustion characteristics of the rocket over a plurality of previously determined combustion efficiencies. The system can then determine those previously determined combustion efficiencies that best match the distance corrected hyperspectral map of the rocket exhaust.

In some embodiments, the information downloaded from the server (302), or entered by the user on the GUI display, can also comprise rocket surface area, rocket construction materials, and the reusability of these rocket construction materials.

To make a more compelling visual display, in some embodiments, the processor can be configured further to retrieve diagrams of the rocket and its engines. The processor can then, for example, use these diagrams to produce one or more enhanced reality images comprising the diagrams of the rocket and its engines. These enhanced reality images can be output with the distance corrected hyperspectral map of the rocket exhaust, output the enhanced reality images to the smartphone's GUI display.

The invention claimed is:

1. A method of determining greenhouse gas emissions during at least some phases of a rocket during flight, said rocket comprising said rocket and rocket exhaust, said method comprising:

using a smartphone configured with a front comprising a GUI display, and a back comprising at least three video cameras, to simultaneously obtain, over a plurality of time intervals, first viewpoint images and second viewpoint images of said rocket and hyperspectral images of said rocket exhaust;

said smartphone further comprising at least one processor, memory, and at least one cellular or WiFi wireless internet connection;

wherein a first said video camera is configured to image said rocket directly, thus creating first viewpoint images;

wherein a second said video camera is configured to image said rocket using a periscope attachment, thus creating second viewpoint images, wherein said periscope attachment is configured to increase a spatial separation between said first viewpoint images and said second viewpoint images;

wherein a third video camera is configured to image said rocket using a spectrum dispersion device, thus obtaining spectrally convoluted images of said rocket and spectrally convoluted images of said rocket exhaust;

using said at least one processor, image recognition software, and said first viewpoint images and said second viewpoint images to determine a distance between said smartphone and said rocket and said rocket exhaust, and as well as images of said rocket and said rocket exhaust;

using said at least one processor, said spectrally convoluted images of said rocket and said spectrally convoluted images of said rocket exhaust, said images of said rocket, and said distance to deconvolute said spectrally convoluted images of said rocket and said rocket exhaust, thus producing a distance corrected hyperspectral map of said rocket exhaust;

using said image recognition software, said images of said rocket, and said distance to said rocket to retrieve information pertaining to rocket types from a database, thus identifying a type of said rocket, a rocket fuel type of said rocket, and fuel combustion characteristics of said rocket;

using said at least one processor, type of said rocket, said distance, and said images of said rocket over a plurality of time intervals to determine a velocity of said rocket over at least some of plurality of time intervals;

using said at least one processor, said type of said rocket, said rocket fuel type, said fuel combustion characteristics of said rocket, and said distance corrected hyperspectral map to determine a combustion efficiency of said rocket over at least some of said plurality of time intervals;

over at least some of said plurality of time intervals, using said at least one processor, said velocity, said rocket fuel type, said combustion efficiency, and a Tsiolkovsky rocket equation, to determine an amount of greenhouse gases emitted by said rocket over at least some of said time intervals and rocket velocities;

and displaying said amount of greenhouse gases on said GUI display.

2. The method of claim 1, wherein said periscope attachment and said spectrum dispersion device are mounted on a case, and said case is configured to detachably snap over at least three said video cameras and over said back, thus positioning said periscope attachment over a second video camera, and positioning said spectrum dispersion device over said third video camera.

3. The method of claim 2, wherein said spectrum dispersion device comprises any of a prism and a diffraction grating.

4. The method of claim 1, wherein said at least one processor uses at least one said first viewpoint images, at least one said second viewpoint images, and a parallax algorithm to determine any of said distance and a volume distribution of said rocket exhaust.

5. The method of claim 1, wherein said at least one processor uses any of said at least one said first viewpoint images, and said second viewpoint images, and at least one spectrally convoluted image of said rocket and said rocket exhaust, and a deconvolution algorithm, and said distance to determine said distance corrected hyperspectral map of said rocket exhaust.

6. The method of claim 1, wherein said at least one processor further analyzes said distance corrected hyperspectral map of said rocket exhaust to determine any of a distance corrected chemical composition map of said rocket exhaust, and a distance corrected temperature composition map of said rocket exhaust;

wherein said at least one processor further analyzes any of said distance corrected chemical composition map of said rocket exhaust, and distance corrected temperature composition map of said rocket exhaust, using any of a formula or database of chemical composition and/or temperature versus said combustion efficiency for said rocket fuel type, and then calculates said combustion efficiency of said rocket over at least one time interval.

7. The method of claim 1, wherein said at least one processor uses said wireless internet connection to retrieve said information pertaining to said rocket types from a remote internet database.

8. The method of claim 1, wherein said information pertaining to said rocket types is entered onto said GUI display by a human user.

9. The method of claim 1, used to monitor greenhouse gas during any of an ascent and a descent of said rocket.

10. The method of claim 1, wherein said processor further sums up said amount of greenhouse gases over said plurality of time intervals from a launch of said rocket to a predetermined speed or altitude; or wherein said processor further sums up said amount of greenhouse gases from a predetermined rocket entry speed or rocket entry altitude to a landing of said rocket.

11. The method of claim 1, wherein said periscope attachment has a length of at least six inches, and is configured to increase a spatial separation between said first viewpoint images and said second viewpoint images by at least six inches; and wherein said periscope attachment further comprises a periscope lens arrangement configured to adjust a magnification of said second viewpoint images to match a magnification of said first viewpoint images.

12. The method of claim 1, wherein said greenhouse gases comprise any of carbon dioxide and methane.

13. The method of claim 1, wherein said processor further uses said type of said rocket to retrieve diagrams of said rocket and its engines;

said processor further calculates at least one enhanced reality image comprising said diagrams of said rocket and its engines, combined with said distance corrected hyperspectral map of said rocket exhaust, and outputs said at least one enhanced reality image to said GUI display.

14. The method of claim 1, therein said Tsiolkovsky rocket equation is:

$$\Delta v = I_{sp} g_0 \ln \frac{m_0}{m_f},$$

where $\Delta v$ is a change in said velocity between between a first-time interval and a second time interval;

$I_{sp}$ is a specific impulse of said rocket;

$m_0$ is an initial mass of said rocket;

wherein and said processor solves for a final mass $m_f$ at said second time interval; and wherein an amount of fuel expended between said first time interval and said second time interval is $m_0-m_f$.

15. The method of claim 14, wherein said amount of greenhouse gasses emitted by said rocket is determined by using said processor to multiply said combustion efficiency of said rocket by said amount of fuel expended.

16. The method of claim 1, wherein said combustion efficiency is determined by using said processor to compare said distance corrected hyperspectral map of said rocket exhaust against a plurality of reference hyperspectral data of said rocket fuel type, and said fuel combustion characteristics of said rocket over a plurality of previously determined combustion efficiencies, and determining those previously determined combustion efficiencies that best match said distance corrected hyperspectral map of said rocket exhaust.

17. The method of claim 1, wherein said information pertaining to said rocket types further comprises rocket surface area, rocket construction materials, and the reusability of said rocket construction materials.

18. The method of claim 1, wherein said smartphone further comprises a GPS sensor and a three-axis accelerometer; and wherein said smartphone uses location data from said GPS sensor and tilt data from said three-axis accelerometer to compute said distance.

19. A method of determining greenhouse gas emissions during at least some phases of a rocket during flight, said rocket comprising said rocket and rocket exhaust, said method comprising:

using a smartphone configured with a front comprising a GUI display, and a back comprising at least three video cameras, to simultaneously obtain, over a plurality of time intervals, first viewpoint images and second viewpoint images of said rocket and hyperspectral images of said rocket exhaust;

said smartphone further comprising at least one processor, memory, and at least one cellular or WiFi wireless internet connection;

wherein a first said video camera is configured to image said rocket directly, thus creating first viewpoint images;

wherein a second said video camera is configured to image said rocket using a periscope attachment, thus creating second viewpoint images, wherein said periscope attachment is configured to increase a spatial separation between said first viewpoint images and said second viewpoint images;

wherein a third video camera is configured to image said rocket using a spectrum dispersion device, thus obtaining spectrally convoluted images of said rocket and spectrally convoluted images of said rocket exhaust;

wherein said periscope attachment and said spectrum dispersion device are mounted on a case, and said case is configured to detachably snap over at least three said video cameras and over said back, thus positioning said periscope attachment over a second video camera, and positioning said spectrum dispersion device over said third video camera;

using said at least one processor, image recognition software, and said first viewpoint images and said second viewpoint images to determine a distance between said smartphone and said rocket and said rocket exhaust, and as well as images of said rocket and said rocket exhaust;

using said at least one processor, said spectrally convoluted images of said rocket and said spectrally convoluted images of said rocket exhaust, said images of said rocket, and said distance to deconvolute said spectrally convoluted images of said rocket and said rocket exhaust, thus producing a distance corrected hyperspectral map of said rocket exhaust;

using said image recognition software, said images of said rocket, and said distance to said rocket to retrieve information pertaining to rocket types from a database, thus identifying a type of said rocket, a rocket fuel type of said rocket, and fuel combustion characteristics of said rocket;

using said at least one processor, type of said rocket, said distance, and said images of said rocket over a plurality of time intervals to determine a velocity of said rocket over at least some of plurality of time intervals;

using said at least one processor, said type of said rocket, said rocket fuel type, said fuel combustion characteristics of said rocket, and said distance corrected hyperspectral map to determine a combustion efficiency of said rocket over at least some of said plurality of time intervals;

over at least some of said plurality of time intervals, using said at least one processor, said velocity, said rocket fuel type, said combustion efficiency, and a Tsiolkovsky rocket equation, to determine an amount of greenhouse gases emitted by said rocket over at least some of said time intervals and rocket velocities;

therein said Tsiolkovsky rocket equation is:

$$\Delta v = I_{sp} g_0 \ln \frac{m_0}{m_f},$$

where $\Delta v$ is a change in said velocity between between a first-time interval and a second time interval;

$I_{sp}$ is a specific impulse of said rocket;

$m_0$ is an initial mass of said rocket;

wherein and said processor solves for a final mass $m_f$ at said second time interval; and wherein an amount of fuel expended between said first time interval and said second time interval is $m_0 - m_f$;

wherein said combustion efficiency is determined by using said processor to compare said distance corrected hyperspectral map of said rocket exhaust against a plurality of reference hyperspectral data of said rocket fuel type, and said fuel combustion characteristics of said rocket over a plurality of previously determined combustion efficiencies, and determining those previously determined combustion efficiencies that best match said distance corrected hyperspectral map of said rocket exhaust;

and displaying said amount of greenhouse gases on said GUI display;

wherein said processor further uses said type of said rocket to retrieve diagrams of said rocket and its engines;

said processor further calculates at least one enhanced reality image comprising said diagrams of said rocket and its engines, combined with said distance corrected hyperspectral map of said rocket exhaust, and outputs said at least one enhanced reality image to said GUI display.

* * * * *